United States Patent [19]

Dahms

[11] Patent Number: 4,624,857

[45] Date of Patent: Nov. 25, 1986

[54] METHOD FOR AUTOMATIC CONTROL OF GALVANIC DEPOSITION OF COPPER COATINGS IN GALVANIC ACID COPPER BATHS

[75] Inventor: Wolfgang Dahms, Berlin, Fed. Rep. of Germany

[73] Assignee: Schering Aktiengesellschaft, Berlin and Bergkamen, Fed. Rep. of Germany

[21] Appl. No.: 698,422

[22] Filed: Feb. 4, 1985

[30] Foreign Application Priority Data

Feb. 3, 1984 [DE] Fed. Rep. of Germany ....... 3404267

[51] Int. Cl.[4] .............................................. C25D 3/38
[52] U.S. Cl. ....................................... 427/8; 204/52.1; 427/10
[58] Field of Search ................... 427/8, 10; 204/52 R

[56] References Cited

U.S. PATENT DOCUMENTS

| | | | |
|---|---|---|---|
| 3,506,546 | 4/1970 | Semienko et al. | 204/52 R |
| 3,969,928 | 7/1976 | Arlow | 427/10 |
| 4,181,582 | 1/1980 | Dahms | 204/52 R |
| 4,315,518 | 2/1982 | Sayer | 137/3 |
| 4,331,702 | 5/1982 | Hieber et al. | 427/10 |
| 4,350,717 | 9/1982 | Araki et al. | 427/8 |

Primary Examiner—Thurman K. Page
Attorney, Agent, or Firm—Michael J. Striker

[57] ABSTRACT

In a method for an automatic control of the galvanic deposition of copper coatings in acid copper bath by measuring a maximal current density and a continual dosing of gloss additives to the bath, the maximal current density is measured by cyclically measuring an actual voltage in the bath and compensating for eventual deviations of the actual voltage from the nominal value by an automatic dosing of the additives by means of dosing devices.

10 Claims, 6 Drawing Figures

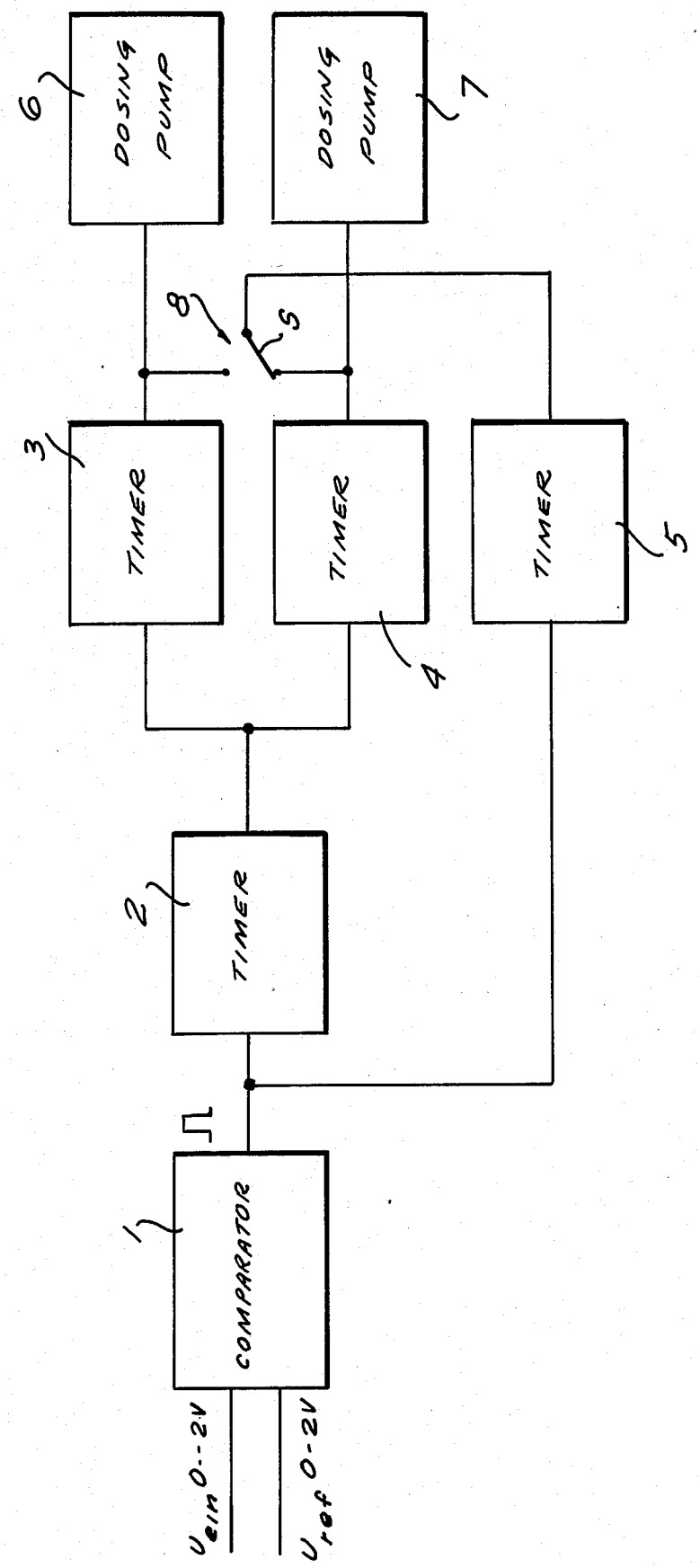
F I G. 1

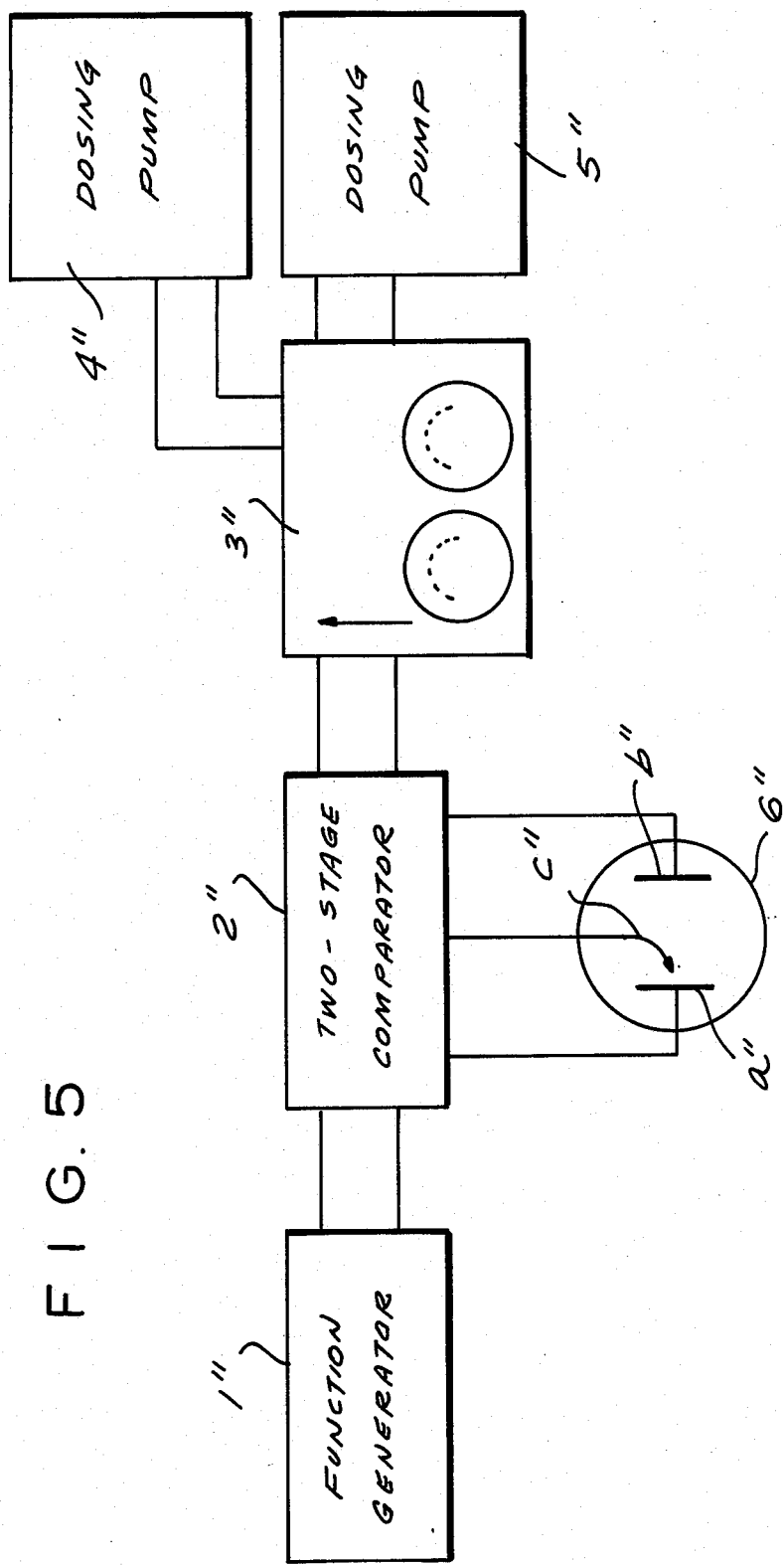
F I G. 5

METHOD FOR AUTOMATIC CONTROL OF GALVANIC DEPOSITION OF COPPER COATINGS IN GALVANIC ACID COPPER BATHS

BACKGROUND OF THE INVENTION

The present invention relates to a method for a fully-automatic control of a galvanic deposition of copper coatings in galvanic acid copper baths.

Galvanic baths, which are particularly used for the deposition of shiny coatings for the strengthening of conductor paths of printed circuits, are during operation subject to a continuous consumption of their substances and must therefore be continually additionally supplied with dosed amounts of materials to be deposited, for obtaining even deposition conditions and to achieve a desired quality of the coatings being deposited. To obtain this it is necessary to preliminarily determine a corresponding metal ion concentration in individual substances of the bath so as to an insufficient or excessive dosing. During the determination of a metal ion concentration by analytical methods or by measuring of conductivity it has been defined that it was necessary to control and restore a required concentration of those substances which carry out such important function as gloss-forming substances or inhibitors.

These substances are also continuously consumed during the current application to the bath; the control of this consumption has been specifically difficult because it has to do with the mixture of a plurality of organic substances which exist in various, and also in very low, concentrations and disaasemble and decompose in accordance with their nature.

One of conventional methods of producing coatings in a galvanic acid copper bath is disclosed in applicant's U.S. Pat. No. 4,181,582.

It has been already proposed to determine an actual condition of the galvanic bath by analytical methods, in which the evaluation of substances has been carried out by a plate-even-integer method or by measuring of voltage ("Plating and Surface Finishing", 65, 1978, 5/60 f, and 69, 1982, 3/62 f). The utilization of these methods has been described in DE-OS No. 2,757,458. With these methods two reference electrolytes must be used; these evaluation methods have been utilized in the galvanic bath, however discontinually, and a continuous working proess with these methods has been impossible.

SUMMARY OF THE INVENTION

It is an object of the present invention to provide a method of a fully-automatic control of the galvanic deposition of copper coatings with the possible best physical properties, by measuring and a continual adding of dosed gloss additives being utilized.

This and other objects of the invention are attained by a method for a full-automatic control of the galvanic deposition of copper coatings in acid galvanic baths by measuring a maximal current density and a continual automatic addition of dosed gloss additives with a determination of deviations of an actual voltage from a nominal voltage value, the method comprising the steps of measuring the maximal current density by cyclically measuring an actual voltage, and eventually compensating for deviations of the actual voltage from the nominal value by means of electronic dosing devices.

A function generator may be used in said measuring step, said function generator cyclically varying a potential between a reference electrode and a rotating platinum disc electrode, between voltage points $-0.2$ V and $+1.8$ V and with a velocity of 100 m V/sec.

The reference electrode may be a silver or silver-chloride electrode.

In the acid galvanic copper bath a peak in the region of the anode or the nominal value, may be $-0.3$ V relative to said silver/silver chloride electrode.

The method may further include the step of examining of the nominal value by an electronic control device which, upon the determination of deviations from a nominal value to define a dosing impulse, sets a dosing pump into operation for supplying the bath with desired gloss additives.

During the electrolysis the voltage peak is smaller and is brought then to a fixed value.

The electronic control devices may include a comparator which compares voltages generated at maximum by a potentiostat during the period of about two cycles This period may be about 1 min. If a desired voltage with a desired polarity does not occur for a short time within the two cycles a dosing impulse for the dosing pump is released.

After the addition of dosed glass additives a waiting time of about two minutes may be maintained for stabilizing the bath, before a further measuring is carried out.

Copper coatings having pH-value $\leq 1$ may be produced in the process.

Usual shiny coatings may be utilized as gloss additives.

The method according to the present invention may be utilized for producing copper coatings with possible best physical qualities, independently from the materials of anodes and cathodes utilized in the bath, for strengthening conductive paths of contact switches and for depositing metal layers on conductors or non-conductors, particularly on printed circuit boards.

The method according to the present invention in a surprising fashion provides a galvanic deposition of copper coatings with possible best physical qualities, and electrical characteristics independently from the materials of the anodes and cathodes in the galvanic bath. A specific technical advantage of the method resides in that a continuous exchange of the type of the cathode and its surface has no influence on the quality of the coatings. The dosing of the gloss additives is carried out in a full-automatic fashion.

The method according to the present invention ensures a uniform copper deposition. Usual disturbances, which occur with conventional methods during the exchange of the type of the cathode, such as in case of a so-called panel-or-pattern plating, or during the operation intervals or during the cleaning of anodes, are avoided. Due to the rapidity of the obtaining of electronic information any changes in the composition of the galvanic bath are defined and compensated for. A portion of annon-used plate, which results during the manufacturing of contact switches by conventional methods, is substantially reduced with the proposed method.

Conventional VA detectors and a VA scanner, as well as known devices for polarography and voltmeters with electronic control and dosing devices, are utilized in the method of the invention.

All electrolytes of known compositions can be used as acid copper baths.

The copper bath may have the following composition:

50–250 g/Liter,
preferably 60–80 g/Liter of copper sulfate (CuSO$_4$.5H$_2$O)
50–250 g/Liter,
preferably 180–250 g/Liter of sulfuric acid
0.05–0.25 g/Liter,
preferably 0.06–0.10 g/Liter of natrium chloride.

In place of copper sulfate other copper salts can be at least partially utilized. Sulfuric acid can be also at least partially replaced by fluorine boric acid. The galvanic bath contains conventional gloss additives.

The operation conditions of the copper bath are as follows:
pH-value: ≦1
Temperature: 15°–35° C., preferably 25° C.
Current density: 0.5 to 8 A/dm$^2$, preferably 2 to 4 A/dm$^2$.

The movement of the electrolyte within the bath is provided by air blast.

The following parameters are used for the control of this method:
First voltage measurement point: −0.1 V to −0.4 V
Second voltage measurement point: +1.6 V to +2.0 V The velocity of the potential charge is 10 to 1000 mV/s, preferably 100 mV/s.

The peak maximum is: +0.335 V±0.07 V.

Simple direct current, such as current $4 \times 10^{-4}$ A is amplified to $I_v$ and extracted.

The working electrode and the counter electrode are made preferably of platinum or platium alloy. The counter electrode can be also formed of copper or copper alloy. The speed of rotation of the working electrode amounts to 500 to 3000 U/min, preferably 2,500 U/min. The diameter of the platinum core is about 3 mm.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWINGS

FIG. 1 is a block diagram illustrating a method of the invention with the use of a comparator;

FIG. 5 is a block diagram of the measuring device of yet another embodiment.

DETAILED DESCRIPTION OF THE PREFERRED EMBODIMENTS

Figure 2:
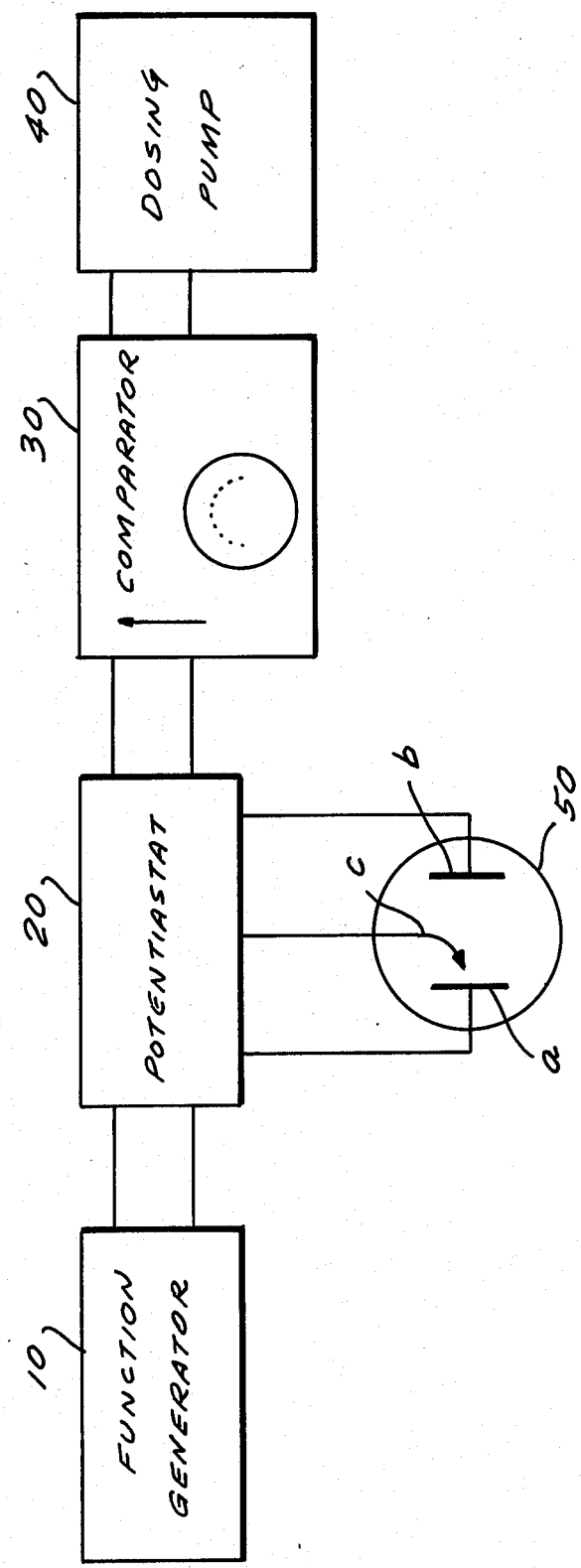
FIG. 2 is a block diagram showing a measuring device.

Referring now to the drawings in detail, and first to FIG. 1, the device for carrying out a method for a full automatic control of electroplating deposition of copper layers in copper acid baths includes a comparator 1 connected to a first timer 2 (40–90 S), which in turn is connected to a second timer 3 (30 sec) and a third timer 4 (1.5 sec) connected in parallel to each other, and also to a fourth timer 5 (2 min). The device further includes a dosing pump 6 and a dosing pump 7 respectively connected to timers 3 and 4. A scanner 8 with a switch S is also provided in the control device. As long as the voltage U$_{ein}$ is > voltage U$_{ref}$ an impulse occurs at each passage of delta voltage, which impulse is reset in timer 2.

If in comparator 1 U$_{ein}$ < U$_{ref}$ no impulses occur. Timer 2 is operated and starts timers 3 and 4 for dosing additives in accordance with respective dosage periods.

The comparator is fed with two different dosage times to close up dosing pumps 6 and 7 of a different type. By means of switch S a dosing period is selected. After selecting a desired dosing time timer 5 is switched on and starts. This prevents, further dosages for time T$_4$ (FIG. 2), for stabilizing the dosing system.

With reference to FIG. 2 it will be seen that the measuring device includes a function generator 10(VA scanner 612), a potentiostat 20 (VA detector 611), a comparator 30, a dosing pump 40 and an electronic element 50 which includes a working electrode a, a counter electrode b and a reference electrode c.

Figure 3:
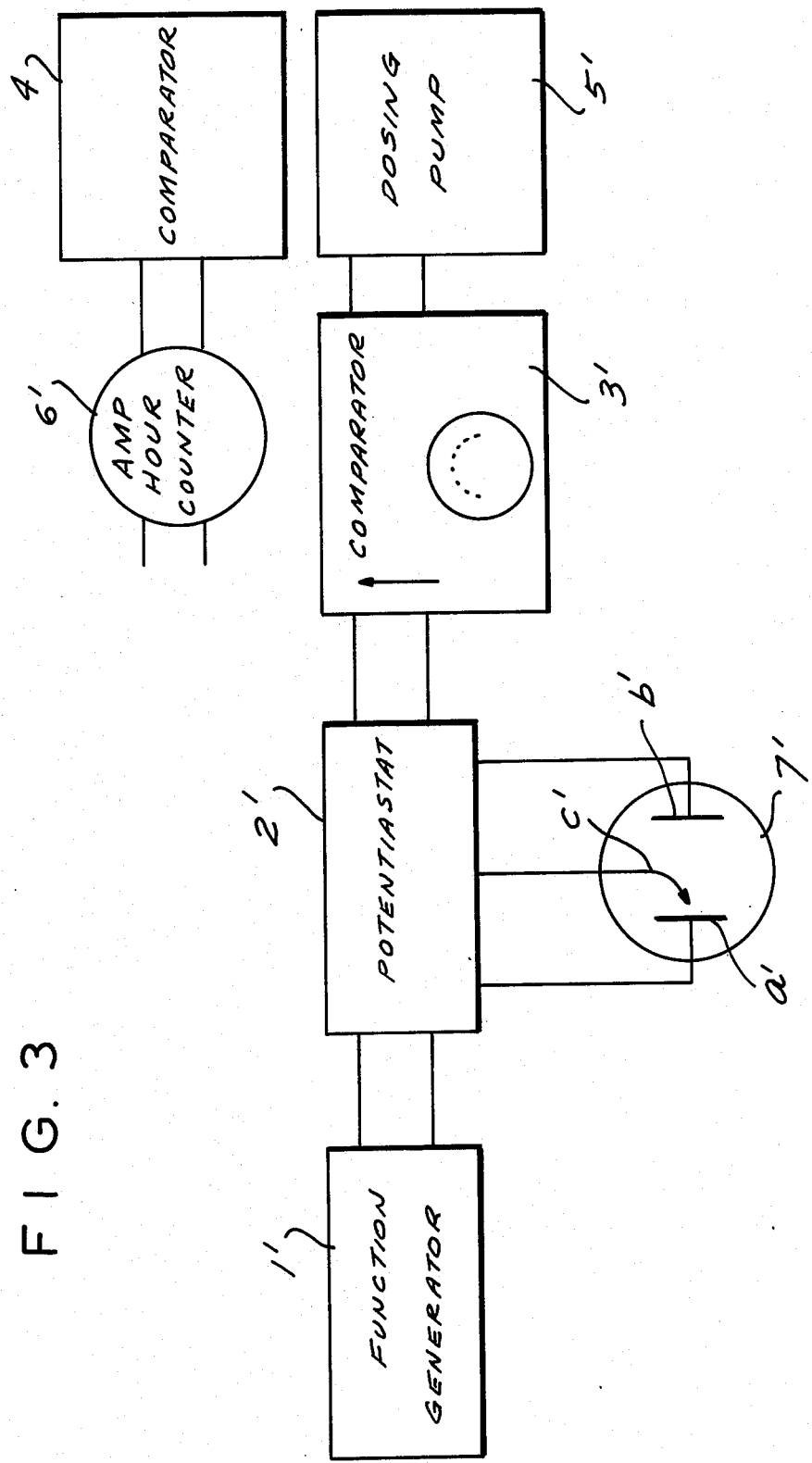
FIG. 3 is a block diagram showing another embodiment of the measuring device with the comparator of FIG. 1, in which a portion of a brightness additive is dosed by an ampere-hour counter.

In FIG. 3 1' is a function generator, 2' is a potentiostat 3' is a comparator, 4' is a dosing pump and 5' is another dosing pump. The measuring device of FIG. 3 further includes an ampere/hour counter 6' and an electronic element 7' which similarly to the embodiment of FIG. 2 includes a working electrode a', a counter electrode b' and a reference electrode 3'.

Figure 4:
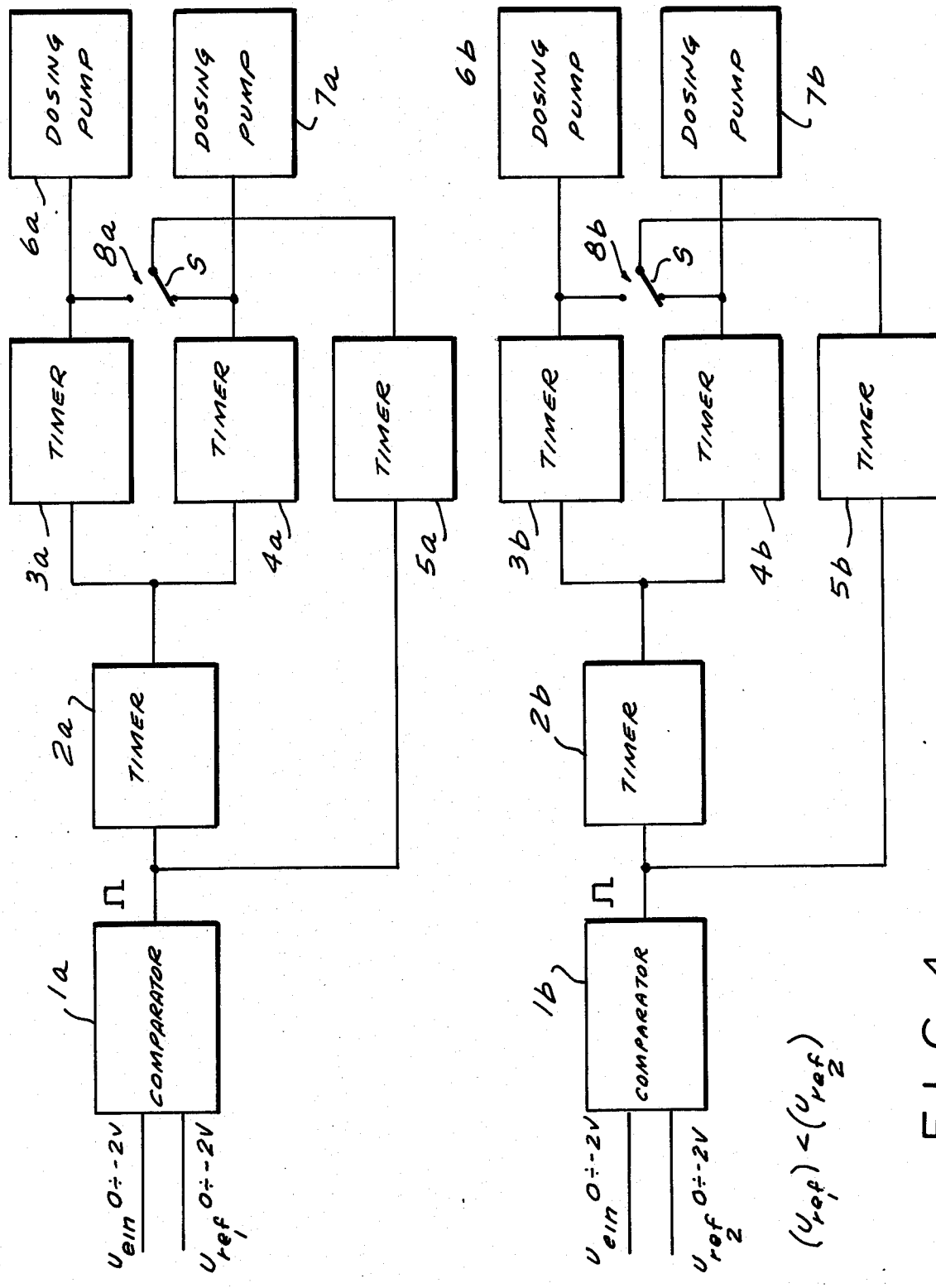
FIG. 4 is a block diagram of another embodiment of the invention, in which a two-stage comparator is utilized.

With reference to FIG. 4 it will be seen that the device for carrying out a control method of this invention of a modified embodiment employs a two-stage comparator. The device includes two comparators 1a, 1b, two first timers 2a, 2b, timers 3a, 4a and 3b, 4b, timers 5a, 5b, dosing pumps 6a, 6b, dosing pumps 7a, 7b and switches 8a, 8b. In this embodiment two reference voltages are provided, wherein U ref$_1$ < Uref$_2$. If U ref$_2$ is exceeded the dosing pump 2b is controlled such that two gloss additives can be additionally dosed.

In FIG. 5 reference numeral 1'' designates a function generator, reference numeral 2'' denotes a two-stage comparator, reference numeral 4'' identifies one dosing pump while reference numeral 5'' is another dosing pump. An electronic element 6'', which is connected to the two-stage comparator, includes a working electrode a'', a counter electrode b'' and a reference electrode c''.

Figure 6:
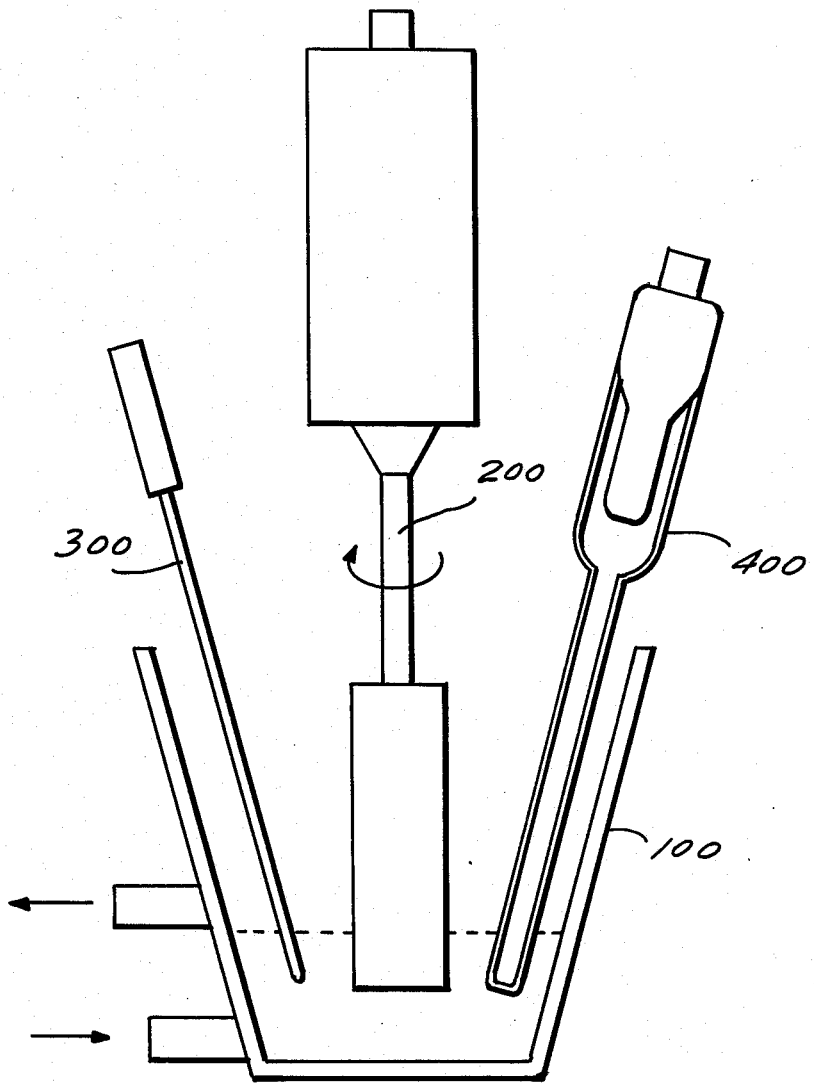
FIG. 6 is a side view of an analyzer.

In FIG. 6, which schematically shows a side view of the electronic measuring element, shown in FIGS. 2, 3 and 5, the measuring element comprises a container 100 which accommodates the end portions of a rotating disc electrode 200, a counter electrode 300 of platinum and a reference electrode 400 made of silver or silver chloride.

In some cases it is expedient to carry out the measurement in accordance with the inventive method in a continually diluted state of the electrolyte wherein the electrolytic solution is diluted with water in ratio 1:9, with an additive-free copper electrolyte in ratio 1:999, diluted sulfuric acid or watery alkaline solutions or alkaline salt solutions.

EXAMPLE 1

A copper bath composition comprised of
80 g/l of copper sulfate (Cu SO$_4$.5H$_2$O) 180 g/l of sulfuric acid (concentrate), and 0.08 g/l of natrium chloride is added with 10 ml/l of a usual gloss bilder on the basis of disulfide/polyglykol.

Copper balls of diameter of 12 mm are selected as anodes. These balls contain 0.04% of phosphorus and are positioned in titanium cages.

The electrolytic bath operates at 2 Ah/l and is supplied with dosed amounts of a suitable gloss builder for 10,000 Ah in accordance with a conventional method. After 10 Ah/l the anodes are removed from the electrolyte for cleaning. Then the process is continued in the same fashion.

An optical appearance or elongation-to-point-of-fracture, or a uniformity of copper extraction in a hole, or a density of a limiting current, each can be selected as a parameter for an estimation.

The results are listed in the following table:

| Change in Ah/l | Appearance | Elongation-to-point-of-fracture properties | uniformity in boreholes | Limiting current A/dm$^2$ |
| --- | --- | --- | --- | --- |
| 0 | weak | 5 | bad | 6.0 |
| 2 | good | 18 | sufficient | 5.5 |
| 4 | weak | 24 | good | 4.5 |
| 6 | good | 20 | good | 5.5 |
| 8 | good | 20 | good | 6.0 |
| 10 | good | 22 | good | 6.0 |
| Cleaning | | | | |
| 12 | weak | 7 | bad | 6.0 |
| 14 | good | 17 | sufficient | 5.5 |
| 16 | weak | 25 | good | 4.5 |
| 18 | good | 20 | good | 5.5 |
| 20 | weak | 21 | good | 6.0 |

The test with the method of the invention is to be repeated. The voltage peak is +350 m V. The dosing of additives is automatically adjusted and amounts to 3.3 kg/10.000 Ah. After the cleaning of anodes, spontaneous deviations in the electrolyte from normal are eventually compensated.

The results are shown in the following table:

| Change in Ah/l | Appearance | Elongation-to-point-of-structure properties | Uniformity of boreholes | Limiting current A/dm$^2$ |
| --- | --- | --- | --- | --- |
| 0 | weak | 5 | bad | 6.0 |
| 2 | good | 18 | sufficient | 5.5 |
| 4 | good | 22 | good | 5.0 |
| 6 | good | 22 | good | 6.0 |
| 8 | good | 22 | good | 6.0 |
| 10 | good | 22 | good | 6.0 |
| Cleaning | | | | |
| 12 | good | 17 | sufficient | 5.5 |
| 14 | good | 22 | good | 6.0 |
| 16 | good | 23 | good | 6.0 |
| 18 | good | 22 | good | 6.0 |
| 20 | good | 23 | good | 6.0 |

The results of the test show that substantially better and uniform quality of products is obtained. Waste is substantially eliminated. The measuring device of FIG. 2 is selected.

EXAMPLE 2

A copper bath having the compsition comprised of
200 g/l of copper sulfate (CuSO$_4$.5 H$_2$O),
60 g/l of sulfuric acid (concentrate) and 0.1 g/l of natrium chloride
is added with a usual gloss substance on the basis of disulfide/polyglykol and 0.5 ml/l of a conventional gloss substance on the basis of safranine ink material. Usual wire bar anodes which are alloyed with 0.04% of phosphorous are utilized in this case.

Firstly 0.5 kg/10 kAh of a gloss additive is added to the electrolyte in accordance with a conventional method. Then a time period of 56 hours is set up. An optical appearance, a leveling and a limiting current density are then evaluated.

The results of the test are listed in the following table:

| Change in Ah/l | Appearance | Leveling % | Density of limiting current A/dm$^2$ |
| --- | --- | --- | --- |
| 0 | good | 60 | 10 |
| 2 | good | 60 | 10 |
| Period 56 hours | foggy | 40 | 6 |
| 4 | almost good | 50 | 8 |
| 6 | good | 60 | 10 |

The test with the method of this invention is repeated. The bath is continually diluted with water in ratio 1:9 and dosed in accordance with the measurements of the device of FIG. 5. The dosing pump 4" is utilized for the first mentioned gloss additive while the dosing pump 5" is used for dosing the second mentioned gloss additive. The peak of the first reference voltage is adjusted to +1500 mv and the second voltage to 1700 mv.

The dosing at the start of the process is adjusted to about 0.5 kg/10 k Ah. After 56 hours defects on both gloss coatings are defined by the control method of this invention. About 0.2 ml/l of the second gloss additive and 0.1 ml/l of the first gloss additive are automatically dosed.

The following table shows the test results:

| Change in Ah/l | Appearance | Leveling | Density of limiting current A/dm$^2$ |
| --- | --- | --- | --- |
| 0 | good | 60 | 10 |
| 2 | good | 60 | 10 |
| Period 56 h | good | 60 | 10 |
| 4 | good | 60 | 10 |
| 6 | good | 60 | 10 |

The method of the present invention provides the improvements in appearance of coated plates, a leveling or flattening of the coating.

It will be understood that each of the elements described above, or two or more together, may also find a useful application in other types of methods for automatic control of electrolytic depositing of copper coatings in acid copper baths differing from the types described above.

While the invention has been illustrated and described as embodied in a method for automatic control of the deposition of copper coatings in acid copper baths, it is not intended to be limited to the details shown, since various modifications and structural changes may be made without departing in any way from the spirit of the present invention.

Without further anlaysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In a method for a full-automatic control of the galvanic deposition of copper coatings in acid galvanic baths by measuring a maximal current density and a continual automatic addition of dosed gloss additives and a determination of deviations of an actual voltage from a nominal voltage value, the improvement comprising the steps of measuring the maximal current density by cyclically measuring an actual voltage, and eventually compensating for deviations of the actual voltage from the nominal value by means of electronic dosing devices, wherein a function generator is used in said measuring step, said function generator cyclically varying a potential between a reference electrode and a rotating platinum disc electrode between voltage points $-0.2$ V and $+1.8$ V and with a velocity of 100 m V/sec.

2. The method as defined in claim 1, and utilized for producing copper coatings with possible best physical qualities independently from the materials of anodes and cathodes utilized in the bath, for strengthening conductive paths of contact switches and for depositing metal layers on conductors or non-conductors.

3. The method as defined in claim 1, wherein said reference electrode is a silver/silver chloride electrode.

4. The method as defined in claim 3, wherein said nominal value is $-0.3$ V relative to said silver/silver chloride electrode.

5. The method as defined in claim 1, further including the step of examining of the nominal value by an electronic control device which, upon the determination of deviations from a nominal value to define a dosing impulse, sets a dosing pump into operation.

6. The method as defined in claim 1, wherein said electronic control devices include a comparator which compares voltages generated at maximum by a potentiostat during the period of about two cycles.

7. The method as defined in claim 6, wherein said period is about 1 min.

8. The method as defined in claim 1, wherein, after the addition of dosed gloss additives a waiting time of about two minutes is maintained for stabilizing the bath, before a further measuring is carried out.

9. The method as defined in claim 1, wherein the copper coatings, having pH-value $\leq 1$, are applied in the method.

10. The method as defined in claim 1, wherein usual shiny coatings are utilized as gloss additives.

* * * * *